United States Patent
Kantam et al.

(10) Patent No.: US 6,320,082 B1
(45) Date of Patent: Nov. 20, 2001

(54) PROCESS FOR ACYLATION OF NAPHTHYL ETHERS

(75) Inventors: Mannepalli Lakshmi Kantam; Mutyala Sateesh; Boyapati Manoranjan Choudary; Kalluri Venkata Sri Ranganath; Kondapuram Vijaya Raghavan, all of Andhra Pradesh (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 09/538,639

(22) Filed: Mar. 30, 2000

(51) Int. Cl.7 .................................................. C07C 45/00
(52) U.S. Cl. .............................................................. 568/319
(58) Field of Search .............................................. 568/319

(56) References Cited

U.S. PATENT DOCUMENTS

| | | | |
|---|---|---|---|
| 5,138,098 | * 8/1992 | Hagen et al. ........................ | 568/323 |
| 5,227,529 | 7/1993 | Neuber et al. ....................... | 568/319 |
| 5,817,878 | * 10/1998 | Spagnol et al. ..................... | 568/319 |
| 5,962,743 | * 10/1999 | Gruber et al. ...................... | 568/319 |
| 6,121,496 | * 9/2000 | Gilbert et al. ...................... | 568/42 |

FOREIGN PATENT DOCUMENTS

| | | |
|---|---|---|
| 9635656 | 11/1996 | (WO) . |
| 9748665 | 12/1997 | (WO) . |

OTHER PUBLICATIONS

English Abstract Of WO 97/48665 Dated Dec. 24, 1997.
English Abstract Of WO 96/35656 Dated Nov. 14, 1996.
Kim, S.D. et al. "The Regioselective Acylation of 2–Methoxynaphthalene to . . . " J. Mol. Catal. A:Chem (2000), 152 pp. 33–45.

* cited by examiner

Primary Examiner—James H Reamer
(74) Attorney, Agent, or Firm—Ladas & Parry

(57) ABSTRACT

An improved process for the preparation of acyl naphthyl ethers useful as important intermediates for drugs, pharmaceuticals and polyesters by reacting a naphthyl ether with a C2–C5 acid anhydride as an acylating agent employing a zeolite beta catalyst is disclosed.

8 Claims, No Drawings

PROCESS FOR ACYLATION OF NAPHTHYL ETHERS

FIELD OF THE INVENTION

The present invention relates to an improved process for the preparation of acyl naphthyl ethers from naphthyl ethers. Acyl naphthyl ethers are important intermediates in the preparation of drugs, pharmaceuticals and polyesters. More particularly, this invention relates to an improved process for the preparation of acyl napthly ethers from naphthyl ethers using C2–C5 acid anhydrides as acylating agents employing zeolite beta as synthesised, microcrystalline or microcrystalline modified zeolite beta.

This invention particularly relates to an ecofriendly process for acylation of naphthyl ethers using acid anhydrides as acylating agents and zeolite beta as catalyst dispensing with the use of stoichiometric amounts of corrosive, toxic aluminum chloride and hydrogen fluoride as Friedel-Crafts reagents. The acylated products are important intermediates for the preparation of drugs and pharmaceuticals and of monomers for polyesters. For example, 6-acetyl-2-methoxynaphthalene or 6-propionyl-2-methoxy naphthalene are intermediates for naproxen, a non-steroidal anti-inflammatory, analgesic, anti-pyretic drug.

BACKGROUND OF THE INVENTION

Reference may be made to U.S. Pat. Nos. 3,803,245 and 3,994,968 wherein acylation of 2-methoxynaphthalene is carried by aluminum chloride in nitrobenzene. The inherent disadvantages in the use of conventional Lewis acid metal chlorides for Friedel-Crafts acylation are that they are non-regenerable and require more than stoichiometric amounts because of strong complexation with the carbonyl product formed. Work-up to decompose the resultant intermediate complex by hydrolysis results in the generation of a large amount of waste product and employment of lengthy, cumbersome and expensive separation process. Reference may be made to U.S. Pat. Nos. 4,593,125 and 4,670,603 wherein naphthyl ethers are acylated with carboxylic acids, carboxylic acid halide or anhydrides in anhydrous hydrofluoric acid. The drawbacks are that hydrofluoric acid is extremely toxic, corrosive, and thus warrants maintenance of stringent safety conditions and requires expensive equipment in order to work with hydrofluoric acid. Further the use of hydrofluoric acid as a solvent, generates large amounts of salts as effluents upon neutralization.

Reference may be made to a publication by Prins et al., Studies in Surface Science and Catalysis, 94, 397, 1995 wherein naphthyl ether in sulfolane solvent is acylated with acetic anhydride using zeolite $H^{30}$-beta obtained through various options. The drawback is that the selectivity towards 6acetyl-2-methoxynaphthalene, a desired regiomer, is poor.

Reference may be made to a publication by Choudary et al., Applied Catalysis A; 171, 159, 1998 wherein aromatic ethers are acylated with acid anhydrides in the presence of metal ion exchanged clays with moderate to good yields. The drawback is that the selectivity towards 6-acetyl-2-methoxynaphthalene is very poor.

Reference may be made to a publication by Holderich et al., Journal of Catalysis, 185, 408, 1999 wherein $H^{30}$-beta zeolite with varying acidic sites obtained through acid treatment was used to effect acylation of naphthyl ether with acetic anhydride in sulfolane solvent. The drawbacks are the yields and selectivities are moderate.

Reference may be made to a U.S. Pat. No. 5,277,529 wherein the acylation of naphthyl ethers with carboxylic acids, anhydrides or chlorides was carried out both in liquid phase and vapour phase employing $H^{30}$ beta zeolite. The drawback is that the yields are poor (9–35%).

OBJECTS OF THE INVENTION

The main object of the present invention is to provide an improved process for the preparation of acyl naphthyl ethers by reacting naphthyl ethers with acid anhydrides aas an acylating agent in the presence of a zeolite beta catalyst which obviates the drawbacks as detailed above.

It is another object of the invention to provide an ecofriendly process for the acylation of naphthyl ethers.

It is another object of the invention to dispense with the use of corrosive and stoichiometric quantities of aluminium chloride and HF.

It is a further object of the invention to provide for the use of zeolite beta synthesised, microcrystalline or microcrystalline modified zeolite beta as catalysts for the acylation of naphthyl ethers.

It is another object of the invention to provide a process for the preparation of acyl naphthyl ethers wherein the selectivity and the yields are good and the work up procedure is simple.

It is another object of the invention to provide a process for the preparation of acyl naphthyl ethers without any disposal problem and wherein the catalyst can be used for several cycles with consistent activity.

It is another object of the invention to provide a process for the preparation of acyl naphthyl ethers, which is economical.

Still another object of the present invention is to use of C2–C5 acid anhydrides selected from acetic anhydride to valeric anhydride as acylating agents.

SUMMARY OF INVENTION

Accordingly, the present invention provides a process for the preparation of acyl naphthyl ethers useful as important intermediates for drugs and pharmaceuticals and polyesters, said process comprising reacting a naphthyl ether with a C2–C5 acid anhydrides as an acylating agent in the presence of zeolite beta catalyst with Si/Al ratio of 4 to 100, in nitrobenzene as solvent at a temperature in the range of 80–180° C. for a period of 2–24 h, and recovering the acylated naphthyl ethers by conventional methods.

In an embodiment of the invention, the zeolite beta catalyst is selected from a synthesised, microcrystalline, or microcrystalline modified zeolite beta.

In another embodiment of the invention the Si/Al ratio of the zeolite beta as synthesised, microcrystalline or microcrystalline modified zeolite beta is preferably 4 to 20.

In a further embodiment of the invention the particle size of microcrystalline zeolite beta is 1 μm to 10 μm.

In another embodiment of the invention, the quantity of the catalyst is 1 to 30% by weight with respect to the substrate.

In still another embodiment of the invention C2–C5 acid anhydrides selected from acetic anhydride to valeric anhydride are used as acylating agents.

In still another embodiment of the invention the reaction is effected at a temperature in the range of 80 to 180° C. for 2–24 hrs.

Yet another object of the present invention is the ratio of naphthyl ether and acylating agent is 1:1 to 1:5.

In another embodiment of the invention, the quantity of the catalyst used is 5 to 30% by weight with respect to the substrate.

DETAILED DESCRIPTION OF THE INVENTION

The novelty of the present invention lies in the use of zeolite beta as synthesised, microcrystalline or microcrystalline modified zeolite beta for the acylation of naphthyl ethers. Decrease in particle size of zeolite beta, enhances the density of acidic sites and surface area of zeolites, which are essential factors to increase the activity of acylation reaction. As a result of this, the space time yields are increased almost three-fold. This is established in the experimental section when compared with the results obtained using micronised and zeolite beta as synthesised. Higher yields and selectivities towards 6-acyl-2-naphthyl ethers are obtained, when zeolite beta as synthesised is used in acylation of naphthyl ethers in nitrobenzene solvent. Since 6-acyl-2-naphthyl ethers are the desired starting materials for the synthesis of naproxen the polyesters, this invention is timely and appropriate. Prior art which used zeolite $H^{30}$-beta offered either low selectivity towards 6-acyl-2-naphthyl ether, a desired intermediate at higher conversions or vice versa. Thus earlier patents fell short of expectations for commercial reality and economics of the process. Therefore, zeolite beta as synthesised is better option, in particular for the synthesis of 6-acyl-2-naphthyl ethers, since it does not encumber post-treatment. The microcrystalline zeolite beta, and $H^+$-microcrystalline zeolite beta, although offered higher conversions in shorter times, the selectivities towards 6-acyl-2-naphthyl ethers are only moderate. However, $Ce^{3+}$-microcrystalline zeolite beta afforded good yields and selectivity towards desired isomer at higher space time yields. Thus, this invention offers the best techno-economic route for the synthesis of 6-acyl-2-naphthyl ethers, intermediates for naproxen and polyesters.

Scientific Explanation

In the present invention, we have used zeolite beta as synthesised, microcrystalline or microcrystalline modified zeolite beta as solid acid catalysts for the acylation of naphthyl ether with C2–C5 acid anhydrides as acylating agents.

In microcrystalline zeolite beta, the density of the acidic sites increases because of increased number of broken edges resulted from the broken aluminium silicate rings. The surface area of these particles is also increased due to reduction of the particle size of zeolites. The higher density of acidic sites eventually increases number of acyl cations generated in the reaction in the electrophilic substitution of the Friedel-Crafts acylation of naphthyl ether and thus enhances activity of the reaction. In fact the activity of these microcrystalline forms is enhanced manifold over normal zeolites.

Higher yields and selectives towards 6-acyl-2-naphthyl ethers are obtained, when zeolite beta as synthesised is used in acylation of naphthyl ethers in nitrobenzene solvent. Since 6-acyl-2-naphthly ethers are the desired starting materials for the synthesis of naproxen and polyesters, this invention is timely and appropriate. Prior art which used $H^{30}$-microcrystalline zeolite beta, offered either low selectivity towards 6-acyl-2-naphthyl ether, a desired intermediate at higher conversions or vica versa. Thus earlier patents fell short of expectations for commercial reality and economics of the process. During the synthesis, zeolite $H^{30}$, dealumination usually occurs, the increased Bronsted sites gained during formation of $H^{30}$ are likely to offset by dealumination process. Therefore, zeolite beta as synthesised is a better option, in particular for the synthesis of 6-acyl-2-naphthyl ethers, since it does not encumber post treatment. The microcrystalline zeolite beta, and $H^{30}$-microcrystalline zeolite beta, although offered higher conversions in shorter times, the selectivities towards 6-acyl-2-naphthyl ethers are only moderate. These lower selectivities are due to the increased external surface area that invariably promotes formation of bulky 1acyl-2-naphthyl ether. However, $Ce^{3+}$-microcrystalline zeolite beta afforded good yields and selectivity towards the desired isomer at higher space time yields. Introduction of the $Ce^{3+}$ increases Lewis acidity of zeolite beta to afford higher selectivity towards 6-acyl-2-naphthyl ethers, because of promotion of the reversible reaction of formed 1-acyl-2-naphthyl ether to naphthyl ether by deacylation.

Zeolite beta, microcrystalline and microcrystalline modified zeolite beta are prepared as in example 1 and employed them in the acylation of naphthyl ethers with acid anhydrides as described in the examples.

The following examples are given by way of illustration of the present invention and therefore should not be construed to limit the scope of the invention.

EXAMPLE 1

Catalyst Preparation a) Zeolite beta:

Tetraethyl orthosilicate and aluminium nitrate of appropriate molar ratios to get desired ratio of Si/Al ranging from 5 to 100 were used. Water is added to tetraethylortho silicate and stirred. To this solution aluminum nitrate, nonahydrate in tetraethylammonium hydroxide solution is added drop wise by a pressure regulating funnel under stirring. After the addition, the solution is kept at 50° C. and later on cooked at 135° C. in an autoclave for one week for crystallization. Then the solid is filtered and air dried. The resultant solid was calcined at 500° C. and used as such.

b) Microcrystalline zeolite beta:

Microcrystalline zeolite beta was obtained by mechanical disintegration of the zeolite beta prepared according to the above procedure (2 $\mu$m to 10 $\mu$m, 95%).

c) Microcrystalline modified zeolite beta 10 g of microcrystalline zeolite beta as synthesised above having Si/Al=15 was subjected to an ion-exchange procedure by stirring with 1 wt % to 5 wt % Ce(III)chloride solution at 80° C. for 6 hours. The resultant zeolite was washed with deionised water and dried at 120° C. After that the metal exchanged zeolite was calcined at 500° C. for 6 hours. e) $H^{30}$-microcrystalline zeolite beta Microcrystalline zeolite beta is added to 1 Molar $NH_4Cl$ solution (10 ml/g zeolite), stirred at 60° C. for 6 hours and the resultant solution was washed with deionised water and dried at 120° C. After that ammonium exchanged zeolite was calcined at 500° C. to get $H^{30}$-microcrystalline zeolite beta.

EXAMPLE 2

A mixture of 2-methoxynaphthalene (10 mmol), acetic anhydride (20 mmol), zeolite beta catalyst as synthesised (0.5 g, calcined at 500° C.) and 5 ml of nitrobenzene solvent were stirred in a round bottomed flask (50 ml) under nitrogen atmosphere at 136° C. temperature. After completion of the reaction (followed by G. C.), the reaction mixture was filtered and distilled to obtain the product. Yield: 1.6 g

EXAMPLE 3

A mixture of 2-methoxynaphthalene (10 mmol), acetic anhydride (20 mmol), zeolite beta catalyst as synthesised (0.5 g, calcined at 750° C.) and 5 ml of nitrobenzene solvent were stirred in a round bottomed flask (50 ml) under nitrogen atmosphere at 136° C. temperature. After completion of the reaction (followed by G. C.), the reaction mixture was filtered and distilled the reaction mixture to obtain the product. Yield: 1.7 g

EXAMPLE 4

A mixture of 2-methoxynaphthalene (10 mmol), acetic anhydride (20 mmol), microcrystalline zeolite beta catalyst (0.5 g) and 5 ml of nitrobenzene solvent were stirred in a round bottomed flask (50 ml) under nitrogen atmosphere at 136° C. temperature. After completion of the reaction (followed by G. C.), the reaction mixture was filtered and distilled the reaction mixture to obtain the product. Yield: 1.6 g

EXAMPLE 5

A mixture of 2-methoxynaphthalene (10 mmol), acetic anhydride (20 mmol), $Ce^{3+}$-microcrystalline zeolite beta (0.5 g) catalyst and 5 ml of nitrobenzene solvent were stirred in a round bottomed flask (50 ml) under nitrogen atmosphere at 136° C. temperature. After completion of the reaction (followed by G. C.), the reaction mixture was filtered and distilled the reaction mixture to obtain the product. Yield: 1.76 g

EXAMPLE 6

A mixture of 2-methoxynapthalene (10 mmol), acetic anhydride (20 mmol), $H^{30}$-microcrystalline zeolite beta catalyst (0.5 g) and 5 ml of nitrobenzene solvent were stirred in a round bottomed flask (50 ml) under nitrogen atmosphere at 136° C. temperature. After completion of the reaction (followed by G. C.), the reaction mixture was filtered and distilled the reaction mixture to obtain the product. Yield: 1.8 g

EXAMPLE 7

A mixture of 2-methoxynaphthalene (10 mmol), propionic anyhdride (20 mmol), zeolite beta catalyst as synthesied (0.5 g) and 5 ml of nitrobenzene solvent were stirred in a round bottomed flask (50 ml) under nitrogen atmosphere at 150° C. After completion of the reaction (followed by G. C.), the reaction mixture was filtered and distilled the reaction mixture to obtain the product. Yield: 1.6 g

EXAMPLE 8

A mixture of 2-methoxy naphthalene (10 mmol), propionic anhydride (20 mmol), microcrystalline zeolite beta catalyst (0.5 g) and 5 ml of nitrobenzene solvent were stirred in a round bottomed flask (50 ml) under nitrogen atmosphere at 156° C. After completion of the reaction (followed by G. C.), the reaction mixture was filtered and distilled the reaction mixture to obtain the product. Yield: 1.8 g

TABLE 1

Acetylation of 2-methoxynaphthalene with various modified zeolite beta catalysts.

| Example No. | Catalyst | Time(h) | Isolated yields[a] (%) | Product distribution[b] | |
|---|---|---|---|---|---|
| | | | | 1-Ac-2Mn | 6-Ac-2Mn |
| 2 | Zeolite beta[c] | 12 | 82 | 18 | 82 |
| 3 | Zeolite beta[d] | 12 | 86 | 26 | 74 |
| 4 | Microcrystalline zeolite beta[c] | 4 | 81 | 35 | 65 |
| 5 | $Ce^{3+}$-microcrystalline zeolite beta[c] | 4 | 88 | 22 | 78 |
| 6 | $H^+$-microcrystalline zeolite beta[d] | 4 | 90 | 31 | 69 |
| 7 | Zeolite beta[c] | 12 | 75[e] | 8 | 92 |
| 8 | Microcrystalline zeolite beta[c] | 4 | 86[e] | 25 | 75 |

[a]based on 2-methoxynaphthalene;
[b]based on H NMR and G.C.;
[c]Calcined at 500° C.;
[d]Calcined at 750° C.;
[e]Acylation with propionic anhydride The main advantages of the present invention are:

1. A novel and ecofriendly process for the acylation of naphthyl ethers.

2. The present process dispenses the use of corrosive and stoichiometric quantities of aluminium chloride and HF.

3. Zeolite beta as synthesised, microcrystalline or microcrystalline modified zeolite beta have been used as catalysts for the acylation of naphthyl ethers.

4. The selectivity and the yields are good.

5. Work-up procedure is simple.

6. The present process envisages no disposal problem as the catalyst can be used for several cycles. The catalyst was subjected to many recycles which displayed consistent activity.

7. The present process is environmentally safe since there is no disposal problem.

8. The process is economical.

We claim:

1. An improved process for the preparation of acyl naphthyl ethers useful as important intermediates for drugs, pharmaceuticals and polyesters, said process comprising reacting a naphthyl ether with a C2–C5 acid anhydride as an acylating agent employing a synthesized, microcrystalline, or microcrystalline modified zeolite beta catalyst with a Si/Al ratio 4 to 100, in nitrobenzene as solvent at a temperature in the range of 80 to 180° C. for a period of 2–24 h, and recovering the acyl naphthyl ethers by a conventional method.

2. A process as claimed in claim 1 wherein the naphthyl ether used is 2-methoxy napthalene.

3. A process as claimed in claim 1 wherein the particle size of microcrystalline zeolite beta is 1 µm to 50 µm.

4. A process as claimed in claim 1 wherein the Si/Al ratio of the zeolite beta as synthesised, microcrystalline zeolite beta and microcrystalline modified zeolite beta is 4 to 20.

5. A process claimed in claim 1 wherein the C2–C5 acid anhydrides used as acylating agents are selected from acetic anhydride to valeric anhydride.

6. A process as claimed in claim 1 wherein the ratio of naphthyl ether and acylating agent is 1:1 to 1:5.

7. A process as claimed in claim 1 wherein the quantity of the catalyst used is 5 to 30% by weight with respect to the substrate.

8. A process as claimed in claim 1 wherein the Si/Al ratio of the zeolite beta as synthesised, microcrystalline and microcrystalline modified zeolite beta is preferably 4 to 20.

* * * * *